United States Patent [19]

Tsukamoto et al.

[11] 4,354,116
[45] Oct. 12, 1982

[54] AUTOMATIC ISOLATOR OF BLOOD PLASMA

[76] Inventors: Shinjiro Tsukamoto, No. 5-31, Utsubohonmachi 3-chome, Nishi-ku, Osaka, Osaka-fu; Masahiro Ugawa, No. 10-12, Hanjo 2-chome, Minoo, Osaka-fu, both of Japan

[21] Appl. No.: 186,087

[22] Filed: Sep. 11, 1980

[30] Foreign Application Priority Data

Sep. 17, 1979 [JP] Japan ................................ 54-119597

[51] Int. Cl.³ ............................................ G01N 15/06
[52] U.S. Cl. .................................. 250/576; 250/577; 73/59; 128/214 E
[58] Field of Search ................. 250/576, 577; 356/39; 73/59; 128/214 E

[56] References Cited

U.S. PATENT DOCUMENTS 4,182,161  1/1980  Greenfield ...................... 356/39 X Primary Examiner—David C. Nelms
Assistant Examiner—Darwin R. Hostetter
Attorney, Agent, or Firm—McGlew and Tuttle

[57] ABSTRACT

An automatic isolator of blood plasma comprising a photosensor to detect the border between the blood plasma layer and that of the blood cells, which have been separated using a centrifugal machine and stored in a blood bag, and a solenoid to stop the transfer of the blood plasma from the blood bag through a tube, by pinching the tube when the border is detected by the photosensor.

4 Claims, 2 Drawing Figures

AUTOMATIC ISOLATOR OF BLOOD PLASMA

BACKGROUND OF THE INVENTION

This invention relates to an automatic isolator of blood plasma out of blood, by detecting the change of the transmittance of visible light at the border between the blood plasma layer and that of the blood cells.

Usually, blood plasma is isolated, using an isolator, for instance HEN-OL type isolator, after separation of the blood cells and blood plasma with a centrifugal machine.

The HEN-OL type isolator is described below. The HEN-OL type isolator has two boards on a base box; one of these boards is fixed at one end of the base box and stands vertically, the other is fastened to rotate around an axis at the same end of the base box.

The rotatable boards is always pushed by a plate spring (not illustrated) toward the vertical board.

A lever is fixed to the rotatable board at the opposite face to the vertical board.

The space between the two boards can be extended, by pushing down the lever and by fastening it at a hook, which protrudes out of the base box.

A bag, which is charged with blood and can be tightly sealing, can be suspended in this space between the two boards, using the hangers on top of the vertical board.

Releasing the lever, the blood bag will be pressed with the rotatable board into the dihendral space, so that the blood plasma can flow out from the blood bag through the tube.

Generally, there is a great difference in these bags as to quantity and in Hematcrik value, which will be abbreviated as H-value. In the conventional method, the blood plasma of a desired H-value, for example 70 or 90, is obtained, by stopping, with a top, the outflow of the blood plasma at the moment when it is visually observed that the border between the two layers reaches the outlet of the blood bag.

When one person operates many isolators of this type, the blood cells frequently intermingle with the isolated blood plasma, as a result of carelessness. Adding to this, the operation is so wearisome, that the number of isolators that can be operated by one person is restricted to two or three.

Blood plasma isolation is necessary within four hours after obtaining blood, for the purpose of producing a blood constituent drug, which request has recently remarkably increased. Now, an efficient isolator of blood plasma with a simplified method to detect the border mentioned above is expected to be developed.

SUMMARY OF THE INVENTION

The object of this invention is to provide an improved efficient isolator as compared to the conventional isolator.

In this method, the rise of the border is detected at the height of a visible light photosensor.

This signal is amplified to drive a solenoid so as to pinch the tube, thereby the transfer of blood plasma is stopped.

Concentrated blood cell liquid having an H-value of 70, or blood cell sediment having an H-value of 90, for example, can be obtained only by setting the photosensor at the H-value scaled on the instrument, which can be normalized by a manufacturer of a blood bag.

Further, by manual operation, it is possible to work temporarily of an H-value of 90 during the producing of H-value of 70 or correct trouble which is caused by a shadow on the photosensor in spite of the compensation using a reference photosensor to prevent such trouble from arising.

BRIEF DESCRIPTION OF THE DRAWINGS:

One of the embodiments of the invention is illustrated in the drawings FIG. 1, FIG. 2.

1: base box; 2: vertical board;
3: rotatable board; 4: lever;
5: hook; 6: hanger;
7: solenoid box; 8: clipper; 9: hinge;
10: long hole; 11: receptacle;
CdS-1: photosensor;
CdS-2: reference photosensor; SW: switch;
PL: pilot lamp; SOL: solenoid;
SCR: Thyristor; TR: timer relay; D: diode;
IC-1: voltage regularator;
IC-2: Operational amplifier.

DETAILED DESCRIPTION OF THE INVENTION

The invention having these purposes is described below with an example of a preferred embodiment.

Figure 1:
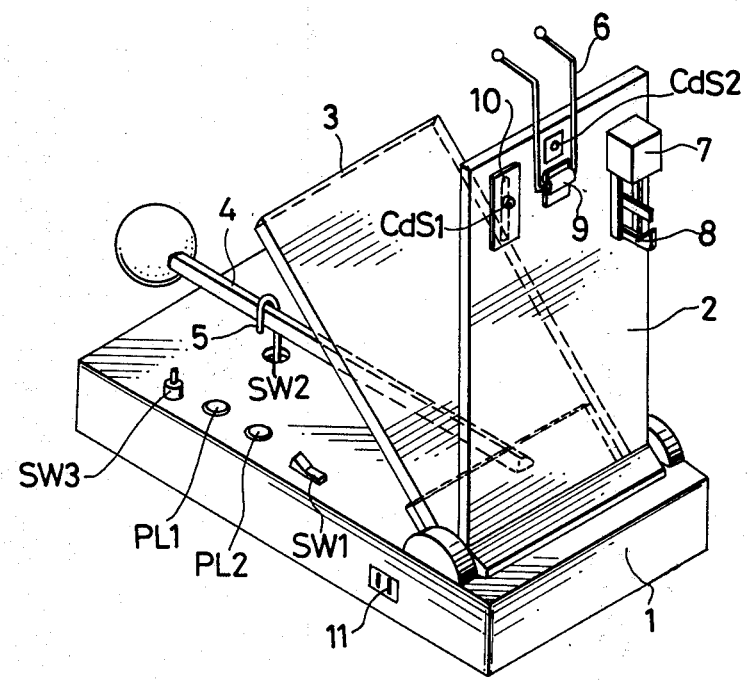
FIG. 1 shows the equilateral view.
Figure 2:
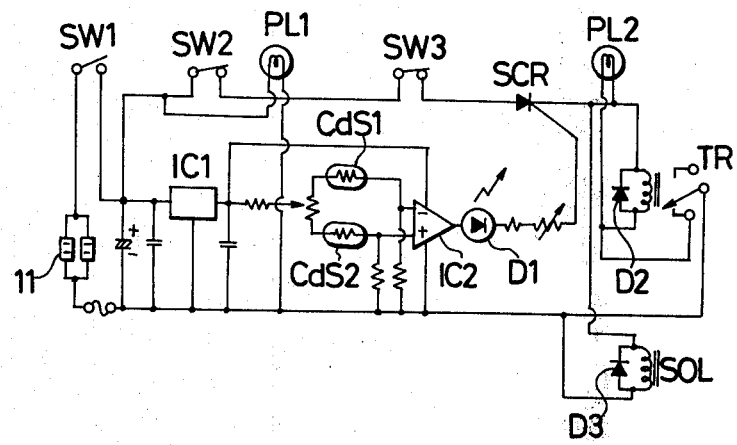
FIG. 2 shows the electric circuit being used in the embodiment.

A case containing the electric circuit shown in FIG. 2 is mounted in the base box I of the HEN-OL type isolator.

A solenoid box 7 containing a solenoid SOL is mounted at one edge of the rear face of the vertical board 2.

A clipper 8 is attached to the bottom of said solenoid box 7 and is driven by the solenoid SOL.

When the clipper 8 is driven by the solenoid SOL, a tube passing through the clipper 8, is pinched to stop the outflow of blood plasma.

The hanger 6 on top of the vertical board can pivot around the hinge 9, for convenience of hanging a blood bag on same.

A photosensor CdS-1 in a case is attached by screws in the vertically long hole 10, which is opened at the other edge of the rear face of said vertical board 2 to detect the border between the two layers, and the height of this hole 10 can be selected to detect the same border.

Another photosensor CdS-2 is fixed at a height of the upper rim of the long hole 10, for reference.

There are found, on the faces of the base box and the vertical board, the elements of the upper rank in the circuit diagram FIG. 2, the power switch SW-1, the stand-by switch SW-3, the manual switch SW-3, pilot lamp (blue) PL-1 and the pilot lamp (red) PL-2; and the elements of the lower rank of the circuit diagram, two receptacles 11, solenoid SOL, photosensor CdS-1 and photosensor CdS-2.

When the lever 4 is pushed down at the hook 5, the stand-by switch SW-2 is opened to open the electric circuit and vice versa.

The receptacles 11 are provided at both sides of the vertical board, for convenience of power supply.

When the manual switch SW-3 is pushed, the electric circuit is opened: same is normally closed.

The following and the functions of the electric circuit.

First, the power switch SW-1 is turned on, then the pilot lamp PL-1 lights up.

Next, the lever 4 is released from the hook 5, then a voltage is applied across the SCR and blood plasma flows out through the tube, because the blood bag is pushed by the rotatable board 3.

As a result of the outflow of the blood plasma, the border between the two layers rises. The rising of the boarder is detected by the photosensor CdS-1, which is positioned at a desired height, to turn on the SCR after amplifying the signal with the operational amplifier IC2.

When the SCR is turned on, the solenoid SOL is driven to pinch the tube, thus the outflow of blood plasma can be stopped at any desired height by means of the photosensor CdS-1.

By the way, even when the tube is pinched and the bag is squeezed by said rotatable board 3, the blood bag will not burst due to its solidarity.

The method for the ordinal H-value, rather low, using the positioning of the photosensor is described above, while the isolations of the blood plasma of the higher H-value is performed manually with the following procedure.

First, the manual switch SW-3 is pushed on to open the circuit so that the solenoid SOL is deenergized and then the clipper 8 is released.

Thus the blood-plasma begins to flow out through the tube.

After a proper length of time, the circuit is closed, by shutting off the manual switch SW-3, and then the solenoid SOL will be driven to pinch the clipper 8, thereby stopping the transfer of blood plasma and the tube is bound up tightly.

Next, the lever 4 is pushed down and fastened at the hook 5 for the opening of the stand-by switch SW-2 to open the circuit.

Consequently, the solenoid SOL is deenergized and the blood bag can be removed from the instrument after removing the tube from the clipper 8.

The invention is applicable not only to the HEN-OL-type isolator, but also to other type isolators in which the rotatable board functions with other means.

The embodiment described here is for the higher H-value.

However, it is possible to apply same to isolate condensed blood cell liquid of any H-value, independently of the H-value and to the quantity of the blood in the blood bag, simply by positioning the photosensor at a desired value which is scaled on the instrument.

Further, with the selection of a height of the photosensor, red blood cell sedimentation, red blood cell suspension, or clean red blood cells can be isolated without having to observe the border of the two layers.

Of course, this invention is applicable to any type of blood bag which is conventionally obtainable.

In this embodiment, CdS is used as a photosensor, but it is compatible with a photosensor of another type having the same effect.

As described above, this invention has solved the faults in the conventional method and is distinguished by the fact that the automatic isolation of blood plasma is performed by comparing the transmittance of light through the blood plasma layer and that of the blood cells.

What is claimed is:

1. An isolator of blood plasma comprising a blood bag having an outlet tube, a photosensor for detecting the border between blood plasma and blood cells in said bag by the change of transmittance of visible light, and which have been separated by centrifugal apparatus, and means responsive to said photosensor for closing said tube so as to stop the outflow of blood plasma.

2. An isolator of blood plasma comprising a photosensor for detecting, by the change of transmittance of visible light, the border between blood plasma and blood cells which have been separated by a centrifugal machine, thereby driving a solenoid to pinch off the tube coming from the outlet of the blood bag so as to stop the outflow of blood plasma.

3. An isolator of blood plasma comprising a photosensor for detecting, by the change of transmittance of visible light, the border between blood plasma and blood cells which have been separated by a centrifugal machine, and an electric circuit amplifying this signal to drive a solenoid, so as to stop the outflow of the blood plasma by pinching off the tube coming from the outlet of the blood bag.

4. An isolator of blood plasma in claim 1, comprising a vertically movable photosensor, which can be adjusted at a height to obtain red blood cells concentrated liquid of a desired H-value.

* * * * *